United States Patent [19]

Vargason

[11] Patent Number: 4,993,271
[45] Date of Patent: Feb. 19, 1991

[54] LIQUID IN SITU MULTIPORT MONITORING SYSTEM

[75] Inventor: Rick D. Vargason, Boise, Id.

[73] Assignee: Micron Technology, Inc., Boise, Id.

[21] Appl. No.: 283,313

[22] Filed: Dec. 12, 1988

[51] Int. Cl.⁵ .................. G01N 15/06; G01N 1/10
[52] U.S. Cl. .................. 73/863.33; 73/61 R; 73/863.23; 356/441
[58] Field of Search .......... 73/863.31, 863.32, 863.33, 73/863.71, 863.72, 863.75, 863.81–863.86, 863.23, 863.24, 863.25, 864.34, 864.35, 864.73, 864.74, 865.5, 61 R, 61 LM, 61.2, 61.3, 61.4, 63, 64; 250/222.2; 134/113; 356/337–343, 441, 442

[56] References Cited

U.S. PATENT DOCUMENTS

| | | | |
|---|---|---|---|
| 3,013,569 | 12/1961 | Sterczala | 134/113 |
| 3,138,015 | 6/1964 | Avery | 73/61 R |
| 3,489,525 | 1/1970 | Natelson | 356/442 X |
| 3,699,802 | 10/1972 | Hotta et al. | 73/863.31 X |
| 3,712,795 | 1/1973 | Hamshere et al. | 356/441 X |
| 3,846,075 | 11/1974 | Cioffi | 73/863.33 X |
| 3,941,563 | 3/1976 | Saltzman | 422/55 X |
| 4,020,676 | 5/1977 | Nuxhall et al. | 210/196 X |
| 4,352,983 | 10/1982 | Silvus, Jr. et al. | 356/70 X |
| 4,758,308 | 7/1988 | Carr | 356/441 X |
| 4,899,767 | 2/1990 | McConnell et al. | 134/99 X |

FOREIGN PATENT DOCUMENTS

| | | | |
|---|---|---|---|
| 10837 | 3/1972 | Japan | 73/61 R |
| 168142 | 12/1981 | Japan | 73/61 R |
| 157527 | 9/1984 | Japan | 73/863.33 |
| 581426 | 11/1977 | U.S.S.R. | 73/61 R |
| 911235 | 3/1988 | U.S.S.R. | 73/61 R |
| 1226823 | 3/1971 | United Kingdom | 73/863.33 |

OTHER PUBLICATIONS

Conference: Proceedings of the 16th Annual Technical Meeting of the Society of Photo-Optical Instrumentation Engineers; vol. 4, San Mateo, Calif., U.S.A., Oct. 16–18, 1972, pp. 131–137, G. J. Wilhelmi et al.; "Remote Water Quality Measurements with a Lider Polarimeter".

Primary Examiner—Tom Noland
Attorney, Agent, or Firm—Stanley N. Protigal; Angus C. Fox, III

[57] ABSTRACT

A method and apparatus for determining the level of particulate contamination in a plurality of liquid sources. The apparatus comprises first and second control valves each having a number of valve elements equal in number to the number of liquid sources, with analytical equipment to determine the amount of particulate contamination in a fluid sample, disposed therebetween. Samples are withdrawn from and returned to the same liquid source. A common valve controller insures that the control valves are maintained at a common valve setting. The analytical equipment is capable of detecting particulate contaminants as small as 0.3 micron.

20 Claims, 1 Drawing Sheet

LIQUID IN SITU MULTIPORT MONITORING SYSTEM

BACKGROUND OF THE INVENTION

Integrated circuit chips are manufactured in a process whereby hundreds of such identical integrated circuits are provided on a single silicon wafer. The integrated circuits are manufactured by a series of "etches", whereby each integrated circuit is covered with a photo-sensitive etch-resistant material (resist), and then light is projected onto each integrated circuit through a photographic stencil, or mask. The exposed resist is then removed chemically (etched) in a chemical solution, leaving a pattern which duplicates that of the mask. Periodically, dopants to control conductivity and sputtered metal to provide interconnection between various layers, are placed onto the integrated circuit.

After each masking step, regardless of its function, excess or undesired material must be etched from the integrated circuit. Because the etching process is a removal of discrete compounds from the exposed surface of the integrated circuit, the etching material accumulates these particulates removed from the surface. Because of the extremely small circuits involved and the small differences in electrical conductivity of the various portions of an integrated circuit, near-absolute purity in the manufacture of such products is required. Any particulate contamination can have extremely adverse affects on the reliability of an integrated circuit. Therefore, extreme measures are undertaken to prevent particulate contamination during the manufacturing process.

Depending upon the particular requirements, an integrated circuit contained on a silicon wafer may undergo as many as twenty or more individual etching steps. Each etch will occur in a different etching solution, to be followed by a rinse in a deionized water bath. The rinse and deionized water baths are arranged in pairs, with, typically, three pairs together in a single hood. Many such hoods are arranged beside one another in a fabrication area. As noted above, the etching step removes material from the integrated circuit, and over time will accumulate in the etch solution and deionize water rinse bath. Both the etch and rinse baths are filtered to remove as much as possible of this particulate contamination. Periodic testing of each of these solutions is required so as to determine if an unacceptable level of contamination exists in either the etch solution or the rinse solution, so that contaminants are not added to the integrated circuit by either of the solutions.

Heretofore, measurement of contamination in the fabrication process was performed relatively infrequently because of the physical limitations of the sampling apparatus available. Typically, contamination of the acid or deionized water was measured when delivered in bulk, and was not subsequently measured in situ during the fabrication process. The obvious problem resulting from this procedure was that if a contamination problem existed, it went undetected for a substantial period of time, thereby resulting in the loss of product produced during such period of excess contamination. An alternative to no testing for contamination whatsoever was a mobile testing unit which could be moved throughout a fabrication area, with samples being manually withdrawn from each acid or deionized water tank for analysis. In addition to the disruption resulting from this process (the station being sampled had to be shut down in order to manually sample each of the baths), such procedure was extremely time consuming and in a large fabrication area each bath may only have been sampled once every few days or weeks. Obviously, excess contamination could therefore ruin a number of days production before discovery.

SUMMARY OF THE INVENTION

In its broadest embodiment, the apparatus of the present invention comprises a closed-loop sampling system whereby a fluid is withdrawn from a fluid bath, analyzed, and returned to the fluid bath. A plurality of baths arranged in close proximity to one another may be sampled sequentially. Generally speaking, the baths are equally divided between etching baths and rinse baths, which are arranged in pairs with from 1-5 pairs per station. Each bath is provided with filter means which, if functioning properly, removes substantially all of the particulate contamination resulting from the etching process.

Specifically, each bath is provided with a conduit which removes a sample from the bath for analysis of particulate contamination. Each bath of a particular station is provided with a conduit, each of the conduits terminating at a first control valve. The first control valve is provided with a number of individual valve means, at least equal in number to the number of baths in the particular station. A single conduit exits from the first control valve and passes through an apparatus capable of measuring the level of particulate contamination in a fluid sample passing through the conduit. After analysis, the fluid sample in the conduit enters a second control valve similar to the first control valve, in that it is provided with a number of individual valve means at least equal in number to the number of baths in the particular station. The sample then returns to the particular bath from which it was withdrawn in a third conduit.

The first and second control valves are controlled by a common valve controller which insures that the particular sample being withdrawn and analyzed is returned to the same bath from which it was withdrawn.

The apparatus and method of the present invention withdraws a relatively small sample, on the order of 25 ml, and returns it to the same bath without causing a disruption in the fabrication process. Results of the analysis for particulate contamination may be automatically recorded in a computer for future analysis of the fabrication process. The common valve controller may be time-controlled such that the various baths are sequentially analyzed, as, for instance, every 1-2 minutes. Recording of data from the analysis may likewise be entered and correlated to a particular bath based upon the time of analysis.

BRIEF DESCRIPTION OF THE DRAWINGS

The drawing is a schematic illustration of the process and apparatus of the present invention.

DETAILED DESCRIPTION OF THE INVENTION

Figure 1:
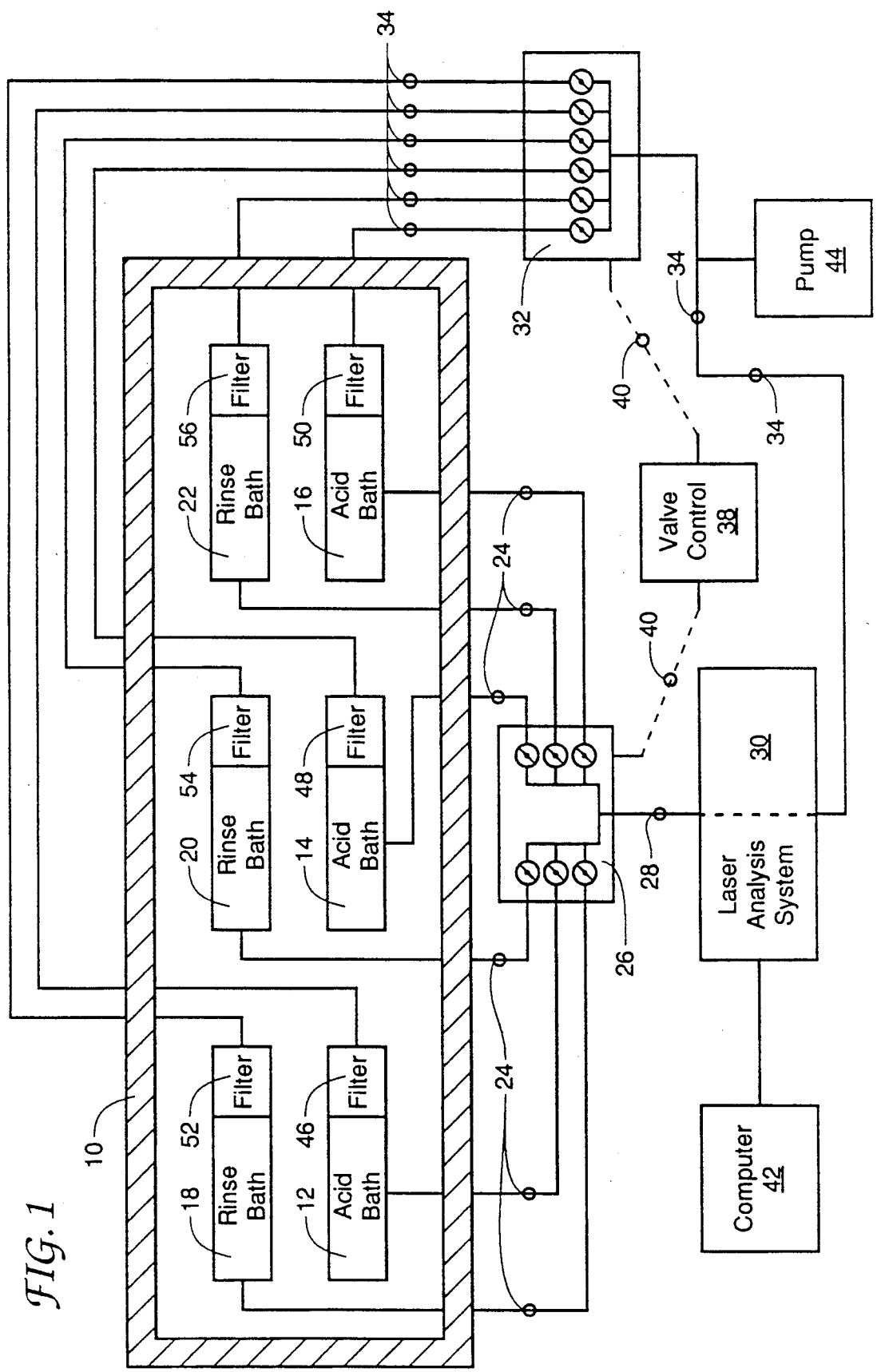

The apparatus of the present invention will be described herein relative to the manufacture of integrated circuits in a conventional fabrication process. It is to be understood, however, that the instant process is applicable to sampling in many other environments as well. Such process requires the repeated etching of a silicon wafer in a plurality of etching or doping tanks, followed by rinse with deionized water. As used hereinafter, the term "etch" or "etching" shall refer to any of the various steps in the process of the manufacture of an integrated circuit wherein material is applied to the surface of the integrated circuit, and then selectively removed.

Etch and rinse tanks are typically paired with one another and a plurality of such pairs are contained within a vented hood capable of discharging noxious vapors resulting from the process. As shown schematically in FIG. 1, the hood, generally designated 10 is illustrated as having six discrete baths therein: three acid baths 12, 14, 16 and three rinse baths 18, 20 and 22, typically containing deionized water. As used hereinafter, "deionized water bath" shall refer to any rinse bath intended to remove residual solution from the etch bath remaining on the etched material, as well as any particulate materials removed in the etching process. It is to be understood that the process of the present invention, as illustrated schematically in FIG. 1, can contain any convenient number of baths consistent with good manufacturing processes.

Each of the baths 12-22 is interconnected by first conduit means 24 to a first common control valve 26. The valve 26 is provided with a number of valve elements at least equal in number to the number of conduits 24. A fluid sample is withdrawn one of baths from 12-22 through conduit 24 and enters the first control valve 26. A first control valve outlet conduit 28 connects the first control valve to an analytical means 30 capable of measuring the level of particulate contamination contained within the fluid sample provided to the analytical means through conduit 28. After analysis, the fluid sample exits the analytical means 30 and is transferred to the second control valve 32 through conduit means 34. The second control valve 32 is similar to the first control valve 26 in that it is provided with a number of valve elements at least as great as the number of baths 12-22. The fluid sample is returned to the bath from which it was withdrawn through a plurality of second conduit means 36.

The plurality of valve elements contained within the first and second control valves 26, 32 are maintained in the appropriate valve settings by a common valve control 38 which is interconnected with the valves 26, 32 by electrical interconnections 40 well known to those of ordinary skill in the art.

The results of the analysis for particulate contamination resulting from the analytical means 30 may be transferred to and stored within a computer 42, thereby providing easy access to the particulate contamination data over a period of time.

In operation, the process of the present invention finds particular usefulness in the manufacture of integrated circuit chips, wherein a series of "etching" steps are performed. In this process, successive layers of the integrated circuit are added to the previous layers in the form of a stencil, with the excess material being etched from the surface by immersion in, typically, an acid bath. Many such acids are used in the etching process, including hydrofluoric acid, nitric acid, sulfuric acid, hydrochloric acid, Buffered Oxide Etch (BOE) and poly etch. The etching process obviously removes from the integrated circuit a small amount of particulate material which was added to the surface of the integrated circuit in the previous step. It is of critical importance in the manufacture of integrated circuits that all particulate contamination, and especially contaminate particles having a diameter greater than 0.3 micron, be avoided. The electrical interconnections necessary in an integrated circuit chip can be adversely affected by the presence of contaminants. Therefore, each of the acid and rinse baths utilized in the manufacture of integrated circuits is provided with filter means 46, 48, 50, 52, 54 and 56 designed to remove particulate contamination from the acid or wash bath. However, such filters do not necessarily work at 100% efficiency and may in fact not remove particulate contaminants as required.

The primary problem resulting from a failure to remove the particulate contaminants is that, if particulate contaminants are introduced into the integrated circuit through either the acid or rinse baths, such contamination will not be detected until after the integrated circuit has proceeded through the entire manufacturing process, and is electrically tested. Because the testing is performed at the end of the fabrication process, a significant quantity of production may be contaminated before the contamination is noted, resulting in substantial financial losses because of the contamination.

The process and apparatus of the present invention permits analysis of a plurality of acid and rinse baths on an extremely short recycle time so that, in the event filters 46-56 fail to remove minimum levels of contamination, such failure will be detected immediately, the fabrication process can be interrupted, and the problem identified and fixed.

In operation, the common valve controller 38 sets the first and second control valves 26, 32 at the same valve setting so that liquid withdrawn from one of the baths and permitted to flow from valve 26 through the analytical means 30 is returned to the same bath through the second control valve 32. A pump 44 may be placed in any convenient location within the system to provide positive pressure for flow through the system. Preferably, the distance between the valves 26, 32 is as short as possible, thereby minimizing the size of the sample withdrawn from the bath for analysis. Preferably, the sample size is as small as 25 ml.

The analytical means 30 must be capable of detecting and measuring, either in absolute or relative terms, the levels of particulate contamination in different kinds of fluid streams. The apparatus must be capable of detecting particulates having a diameter as small as 0.3 micron. It has been found that an analytical means in the form of a laser, which directs a beam of light through the liquid sample to be measured and thence onto a photoreceptor or photodiode works adequately in the process of the present invention. The amount of light received by the photodiode is directly proportional to the amount of light from the beam absorbed by particulate contamination within the fluid sample. For example, Applicant has found that a PMS Model IMOLV (Integrated Micro-Optical Liquid Volumetric) with PLS is an excellent measuring device for use herein. In this device, the sample fluid stream is directed through a capillary between the A-R window and the capillary lens, such that the shaped laser beam is directed through the capillary to impinge on the photodiode for measurement.

After analysis, the sample is returned to the bath from which it is withdrawn.

By withdrawing a relatively small sample for each analysis (on the order of 25-100 ml), the fabrication process during the manufacture of integrated circuits need not be interrupted. The apparatus of the present invention must be situated in close proximity to the hood, in order to utilize such small sample sizes. The conduits 24 will typically be fully charged, but the system downstream from first control valve 26 will contain fluid from only a single bath, in a quantity small enough to have no appreciable effect on the proper functioning of the bath during the fabrication process.

Obviously, the various components of this system must be selected so that they are impervious to corrosion by the acids and deionized water which are sampled.

The apparatus of the present invention may be adapted to provide the results of the sample analysis to a computer for storage of the data. While any method of data retrieval and storage known to those skilled in the art is acceptable, Applicant has found that a time-based controller works quite well. In other words, if the valve controller is set to sequence through the various valve settings on a timed basis (i.e. every 30 seconds), data storage may be set accordingly. Therefore, the analytical data received by the computer is stored under a particular code or name depending on the time it is received.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

I claim:

1. A method of sequentially analyzing the contamination of a plurality of liquid sources, comprising:
    (a) interconnecting each of the plurality of liquid sources to a first control valve;
    (b) withdrawing a representative stream of liquid from each of the liquid sources;
    (c) controlling the flow from each of the plurality of of liquid sources by separate valve means within the first control valve;
    (d) measuring the particulate contamination of each of the plurality of liquid sources;
    (e) returning the stream of liquid through a second control valve to the respective liquid source; and
    (f) automatically controlling the withdrawal and return of the liquid stream through the first and second control valves with a common controller.

2. The method as recited in claim 1, further comprising the step of withdrawing a liquid stream from each of the liquid sources in sequence.

3. The method as recited in claim 1, further comprising the step of connecting each of the plurality of liquid sources to the first control valve within individual first conduit means affixed to a separate valve means within the first control valve.

4. The method as recited in claim 1, further comprising the step of connecting each of the plurality of liquid sources to a separate valve means in the second control valve with individual conduit means.

5. The method as recited in claim 1, further comprising the step of interconnecting the first and second control valves with a single conduit, the conduit permitting determination of the level of particulate contamination of a liquid passed therethrough.

6. The method as recited in claim 5, further comprising the step of measuring the particulate contamination within the conduit between the first and second control valves.

7. The method as recited in claim 6, further comprising the step of measuring the particulate contamination by the absorption of a laser beam directed through the conduit.

8. The method as recited in claim 1, further comprising the step of withdrawing the stream of liquid from and returning the stream of liquid to the liquid source without substantially effecting the level of the liquid in the liquid source.

9. An apparatus to sequentially analyze the level of contamination of a plurality of liquid sources, comprising:
    a first control valve having separate valve means at least equal in number to the number of the plurality of liquid sources;
    a first plurality of conduits interconnecting each of the plurality of liquid sources to a separate valve means within the first control valve;
    a second control valve having separate valve means at least equal in number to a number of the plurality of liquid sources;
    a second plurality of conduits interconnecting each of the plurality of liquid sources to a separate valve means within the second control valve;
    third conduit means interconnecting the first and second control valves and having means therein to analyze particulate contamination in the third conduit means; and
    control means to automatically control passage of a liquid sample through the first and second control valves such that the liquid sample withdrawn from a liquid source is returned to the same liquid source after analysis.

10. The apparatus as recited in claim 9, wherein the means to analyze for contamination within the liquid source comprises means to measure the absorption of a laser beam by particulate contamination within a liquid sample.

11. The apparatus as recited in claim 9, wherein the control means automatically opens corresponding valve means on each of the first and second control valves simultaneously.

12. The apparatus as recited in claim 11, wherein the control means automatically withdraws liquid samples from each of the plurality of liquid sources one after the other.

13. The apparatus as recited in claim 9, wherein the plurality of liquid sources are filtered to remove contamination therefrom.

14. In a method of analysis of a plurality of filtered liquid baths useful in the sequential step-wise etching of a silicon wafer, wherein the level of particulate contamination of each filtered liquid bath is analyzed, the improvement comprising:
    (a) interconnecting each of said liquid baths to a first control valve to withdraw liquid from each liquid bath, the first control valve having a number of individual valve means at least equal in number to the number of liquid baths;
    (b) interconnecting each of the liquid baths to a second control valve to return liquid to the liquid bath from which it was withdrawn, the second control valve having a number of individual valve means at least equal in number to the number of liquid baths;
    (c) controlling the first and second control valves such that each is open to the appropriate valve means to sequentially withdraw and pump a sample from each liquid bath and return the sample to the liquid bath from which it was withdrawn;

(d) analyzing the sample for particulate contamination by passing the sample through a laser particle sensing device capable of detecting particles as small as 0.3 micron; and (e) compiling the results of step (d) and determining if the liquid baths contain greater than a predetermined minimum level of particulate contamination.

15. The method as recited in claim 14, further comprising the step of providing the components of claim 14 in a material resistant to corrosion by hydrofluoric acid.

16. The method as recited in claim 14, further comprising the step of compiling the results of step (d) on a timed-sequence basis such that data is received from the sensing device and related to a particular liquid bath based upon the time of data generation.

17. The method as recited in claim 14, further comprising the step of providing one-half of the liquid baths as acid-etching baths and one-half of the liquid baths as deionized water baths.

18. The method as recited in claim 17, further comprising the step of analyzing the acid-etching baths and the deionized water baths alternately.

19. The method as recited in claim 14, further comprising the step of filtering the liquid baths to remove particulate contamination therefrom.

20. The method as recited in claim 14, further comprising the the step of withdrawing a sample having a volume of about 25 ml.

* * * * *